United States Patent [19]

Phillips, Jr. et al.

[11] Patent Number: 4,483,791
[45] Date of Patent: Nov. 20, 1984

[54] RECOVERY OF FATTY ACIDS FROM TALL OIL HEADS

[75] Inventors: C. Frank Phillips, Jr.; Dwight E. Leavens, both of Panama City, Fla.

[73] Assignee: Sylvachem Corporation, Panama City, Fla.

[21] Appl. No.: 506,924

[22] Filed: Jun. 22, 1983

[51] Int. Cl.³ .............................................. C09F 1/02
[52] U.S. Cl. ................................... 260/97.7; 260/97.6
[58] Field of Search .............................. 260/97.6, 97.7

[56] References Cited

U.S. PATENT DOCUMENTS

| | | |
|---|---|---|
| 2,175,490 | 10/1939 | Stresen-Reuter et al. ............... 87/16 |
| 2,296,952 | 9/1942 | Ross et al. ............................ 260/97.5 |
| 2,362,888 | 11/1944 | Cox ........................................ 260/97 |
| 2,389,284 | 11/1945 | Turck, Jr. et al. .................. 260/97.5 |
| 2,396,671 | 3/1946 | Auer ..................................... 260/105 |
| 2,802,845 | 8/1957 | Sadler .................................. 260/413 |
| 3,575,952 | 4/1971 | Morris et al. ....................... 260/97.7 |
| 3,804,819 | 4/1974 | Wengrow et al. ................. 260/97.6 |
| 3,887,537 | 6/1975 | Harada et al. ..................... 260/97.6 |
| 4,064,117 | 12/1977 | Leavens et al. .................... 260/97.6 |
| 4,151,160 | 4/1979 | Koebner .............................. 260/97.6 |

Primary Examiner—Herbert S. Cockeram
Attorney, Agent, or Firm—R. A. Sturges; M. H. Douthitt

[57] ABSTRACT

There is provided a process for recovery of fatty acids from tall oil heads comprising the steps of neutralizing the acids with a mixture of a magnesium soap forming compound and an alkali metal soap-forming compound under fusion conditions, stripping out unsaponifiables and springing the fatty acids with a mineral acid.

11 Claims, 2 Drawing Figures

RECOVERY OF FATTY ACIDS FROM TALL OIL HEADS

This invention relates to an improvement in process for recovering heads fatty acids from tall oil heads and more particularly to such process wherein said heads are treated with alkali.

In U.S. Pat. No. 3,887,537 it has been proposed to blend an aqueous solution of caustic soda with such tall oil heads and to heat the resulting mixture to a temperature of about 110° C. for about 20 minutes. The heated mixture then is passed into a thin film evaporator wherein retained water and unsaponifiables are distilled off. Typically, a sufficient proportion of alkali is used to fully neutralize the heads fatty acids present, and often a small excess of alkali beyond this. The aqueous caustic soda and tall oil heads form a fairly intractable mass in such initial cooking operation, tend to foam excessively, and display poor heat transfer characteristics resulting in localized overheating and degradation of the soap. Additionally, a solid may form which can compound the heat transfer problem. This makes the process laborious, difficult, slow, and frequently dangerous.

U.S. Pat. No. 4,064,117, commonly owned with the present application, overcame the problem of difficult handling the heads acids soaps, and enabled the formation of low cost, nontoxic soaps which upon acidulation yielded nontoxic salts. The principal difficulty of the Leavens et al process in U.S. Pat. No. 4,064,117 is that sodium soaps are very viscous even at high temperatures. They are quite viscous at 230° C. and below.

Koebner U.S. Pat. No. 4,151,160 sought to overcome the problem by forming lower melting soaps of zinc or lead, or a mixture of zinc and lead soaps. These soaps are reasonably fluid over a range of 90° to 260° C. The process has the disadvantage, however, of using zinc or lead soaps. These salts are toxic necessitating extra equipment and labor to prevent environmental pollution by either lead or zinc ions.

The present invention seeks to overcome the disadvantages of each of the foregoing processes.

It has been found that by forming the magnesium salts of heads fatty acids, one is working with a non-toxic metal ion which does not present an environmental hazard. Magnesium is also inexpensive enough that it can be discarded after the reaction is over although it can be recovered easily by precipitating as the hydroxide with sodium hydroxide, filtering off the magnesium hydroxide, drying (if desired) and recycling to the head acids treatment process.

Unfortunately, magnesium fatty acid soaps are fairly viscous after the unsaponifiables are stripped partially or completely from the system. It should be noted that there is no problem with viscosity using zinc, sodium, or magnesium as long as the unsaponifiables are present. Viscosity and pumping problems occur when the unsaponifiables are removed.

Generally, after the unsaponifiables are stripped off, zinc salts are pumpable from 90° C. to 280° C. and higher. Sodium salts are pumpable from 230° C. to 280° C. and higher. Magnesium salts are pumpable from 200° C. to 280° C. and higher. Calcium salts would be a likely candidate because of low toxicity and low cost. However, these soaps are so viscous that it is not possible to strip off completely the unsaponifiables.

It was then decided to add back unsaponifiable-free fatty acid to the magnesium soap to lower the viscosity. This technique made the product pumpable and enhances the next step of the process by providing a fluid magnesium soap and fatty acid mixture which can readily react with dilute sulfuric acid at 100° C.

Unfortunately, the magnesium soaps have a problem at stripping temperature where they decompose to form unsaponifiables. It has been found that this problem can be overcome by reacting from 75% to 95% of the available fatty acid in the heads cut with a magnesium soap forming reactant (oxide, hydroxide, carbonate, etc.) and the balance with a sodium soap forming reactant. The alkali metal soap forming compound can be any of the alkali metal (sodium potassium or lithium hydroxides, carbonates or bicarbonates. Sodium hydroxide is preferred. In the absence of the sodium soap, the magnesium soap rapidly decomposes (decarboxylates) at 250° C., but is stable at 230° C. (FIG. 2). By replacing approximately 10% of the magnesium with sodium yields a stable mixture at 250° C. (FIG. 2) and indeed that stability is maintained to temperatures as high as 280° C.

The inclusion of sodium soaps in a magnesium soap system also lowers the viscosity but only to a small degree. The greatest advantages are the nontoxicity of the salts after "springing" the free acid and the stability of the mixture at higher temperatures against decarboxylation, a completely surprising result.

BRIEF STATEMENT OF THE INVENTION

Briefly stated, the present invention is in a process for recovery of fatty acids from tall oil heads which comprises the steps of neutralizing tall oil heads acids with a mixture of from 75 parts to 95 parts of a magnesium soap-forming compound and from 5 to 25 parts of a alkali metal soap-forming compound under fusion conditions, stripping the unsaponifiable moiety at a temperature above 230° C. by evaporation, and springing the heads fatty acids with a mineral acid.

BRIEF DESCRIPTION OF THE DRAWINGS

The invention may be better understood by having reference to the annexed drawings wherein.

DETAILED DESCRIPTION OF THE INVENTION

As indicated above, the process of this invention contemplates treating the heads acids obtained from the distillation of tall oil, by a fusion process with at least two soap-forming agents, one of which forms an alkali metal soap, the magnesium soap being from 75 weight % to 95 weight % of the soaps formed and the alkali metal soap being from 5 wt. % to 25 wt. % of the soaps formed. After soap formation, the "unsaps" are stripped, preferably under vacuum, and thereafter, the acids are "sprung" from the soaps with a mineral acid, e.g., sulfuric, hydrochloric, nitric, or phosphoric. As indicated in the flow sheet, it is desirable to recycle a portion, e.g., 10% to 40% by volume of the recovered fatty acids to the concentrated soap mixture exiting from the "unsap" stripping operation to fluidize the soap and make pumping somewhat easier.

It is convenient at this point to define the terms which are used herein and in the appended claims:

1. Tall Oil Heads: a distillation fraction of light boiling material obtained when tall oil is subjected to fractional distillation. Typically, it consists of a mixture of palmitic, oleic, and linoleic acids ranging from about 50% to 75%, the remainder generally consisting of unsaponifiable material. A substantial proportion of such unsaponifiable material has a boiling point very close to that of the fatty acids, thus rendering separation of fatty acids from unsaponifiable material by fractional distillation commercially unfeasible.

2. Unsaponifiables or "unsaps": that portion of head cuts, including impure organic acids, which will not react with an alkali metal agent when heated in a mutual solvent, usually ethyl alcohol or methyl alcohol. In the case of tall oil heads cuts, the unsaponifiables generally are believed to be long chain alcohols, aldehydes, rosin degradation products, and dimethoxystilbene.

3. Alkali metal agent: the hydroxide, oxide, carbonate, and bicarbonate of the metals sodium and potassium.

4. Alkali fusion cook: that chemical reaction wherein a fatty acid is reacted with an alkali metal agent at elevated temperature sans the addition of water to form (a) fatty metallic salt and water when the agent is an alkali metal hydroxide or oxide, or (b) the fatty metallic salt, water, and carbon dioxide when the alkali metal agent is an alkali metal carbonate or bicarbonate.

5. Heads fatty acid: the fatty acid typical of tall oil heads comprising largely palmitic, oleic, and linoleic acids.

6. Springing (acidulation): that chemical process wherein fatty acid salts are treated with a mineral acid to convert said salts to their corresponding fatty acids. A spent aqueous phase and a fatty acid phase will form upon springing water-insoluble fatty acids from their corresponding salts.

7. Hydrating: for present purposes, hydrating means dissolving the anhydrous fatty acid soap in water in preparation for springing their corresponding fatty acids.

Figure 1:
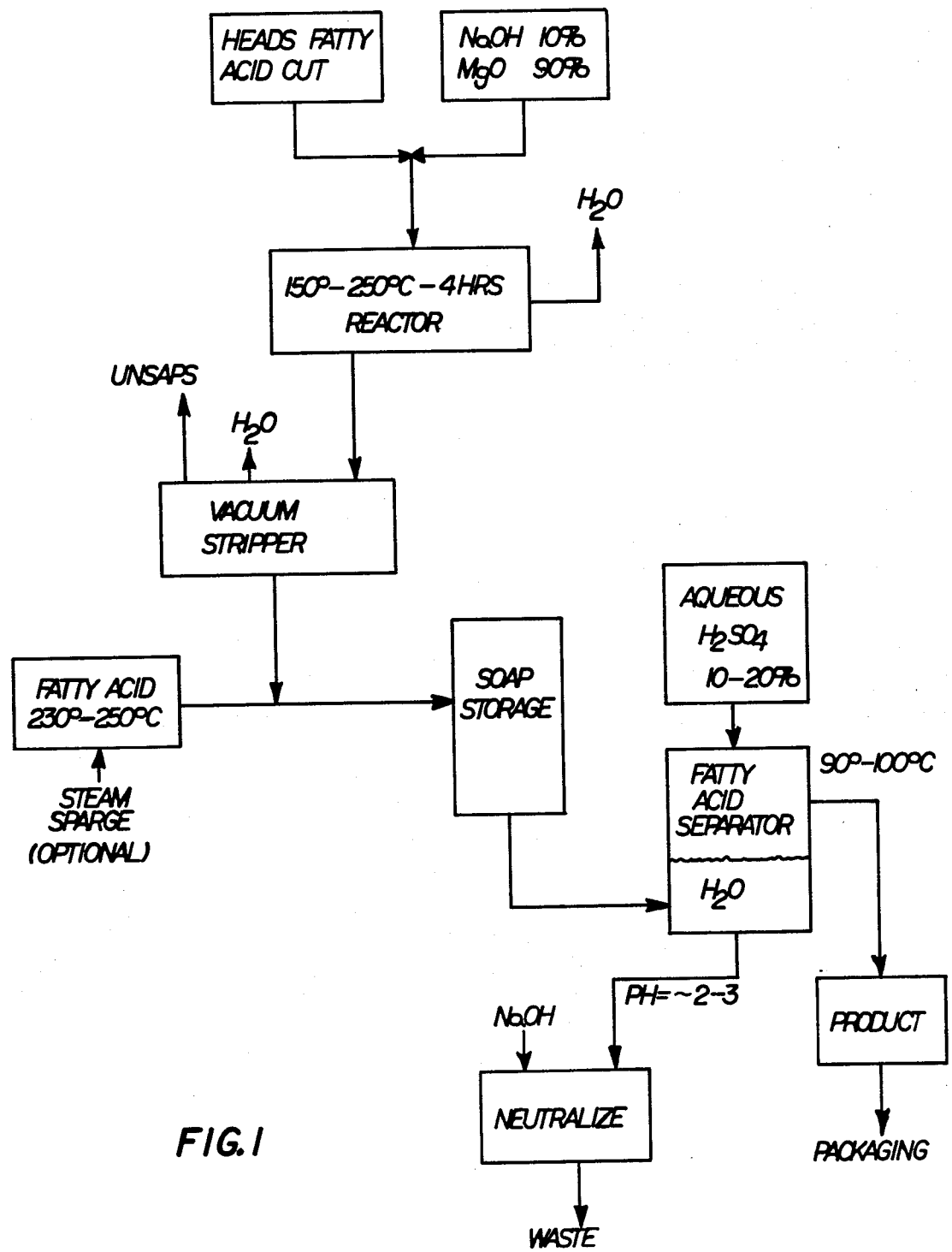
FIG. 1 is a flow diagram for a preferred embodiment of the invention.

Referring now to FIG. 1, there is illustrated by flowsheet diagram a preferred process in accordance herewith. The heads acids are obtained by fractional distillation of tall oil. These acids are largely composed of oleic, palmitic and linoleic acids (about 75%) and the remainder is unsaponifiable material which is very difficult to separate from the heads. The acid number is about 130, and two-thirds of the material is acid and the balance "unsaps", hydrocarbons and sterols. The heads including the "unsaps" are placed in a heated vessel able to withstand reduced pressure and a mixture of alkali metal hydroxide and magnesium oxide dry powder added. The combined amount of the basic reacting soap-forming agents is stoichiometrically related to the fatty acid content of the heads and is, therefore, between 0.5 and 1:1 on a mole basis. The proportion of alkali metal soap forming agent to magnesium soap-forming agent is adjusted such that the combined heads acids soap content is from 5% to 25% by weight alkali metal soap and the balance magnesium soap, e.g., as shown 10% NaOH and 90% MgO. Because of the closeness of the molecular weights, these weight %'s correspond closely to the mole %'s.

Alkali metal agent includes the hydroxide, oxide, carbonate, and bicarbonate of sodium and potassium. Advantageously, the alkali metal agent is alkali metal hydroxide and for efficiency and economy preferably it is sodium hydroxide (caustic soda) in solid lump or pellet form. Advantageously, the sodium hydroxide should have a purity of at least 80% with only incidental water of at most about 10% and generally lower, for example, 5 to 0%. The total water entering the initiation of the fusion cook from all sources—heads, caustic soda, and adventitious sources—should not be substantially more than about 12% of the total initial reaction mixture, and preferably not more than about 8% for suppressing intractability of the reaction mass. During fusion cook water is formed, and much of it distills off.

Fusion is conducted at about 160° C. to 300° C. preferably between about 200° and 260° C., e.g., 230° C. for a period of time to substantially react all the added soap forming agents, e.g., 4 hours. Water is a by-product of the reaction and is continuously removed by gradually reducing the pressure from atmospheric. Desirably the water content is reduced below about 12% in the reaction mass. When the reaction has virtually terminated as evidenced by little or no evolution of water, the vacuum is drawn down until the unsaponifiables are distilled over. This stripping operation is not complete albeit effective and economical. The charge is then dumped into a continuous wiped film evaporator where the remaining "unsaps" are removed.

The soaps are then dumped (while at an elevated temperature (230° C. to 260° C.) into a storage tank and blended with 25% by volume recycle purified fatty acid product to improve the fluidity of the soap mass. The material during storage may be sparged with steam. The soaps are solid at room temperature.

On demand, the soaps are pumped to a "springing" tank where they are mixed with an aqueous solution of a mineral acid, preferably sulfuric acid of about 9°–18° (Baume). This treatment is run at 90° to 100° C. and quickly results in the formation of two layers which separated easily and cleanly. The heads fatty acid product above, and an aqueous medium below had a pH of about 2 to 3. The fatty acid product has a color of about 18 Gardner-Holdt. A portion of the product is desirably recycled to improve pumpability as above described.

The aqueous layer is neutralized with sodium hydroxide and can be sewered directly. This medium contains no lignins and has a low B.O.D.

Materials of construction should be quite resistant to the substances being handled. Thus, advantageously, materials of construction for the fusion cook reactor and distillation include, for example, black iron and stainless steel; for the hydration black iron, stainless steel and glass; and for the acid springing stainless steel and glass.

The following example shows how this improvement has been practiced, but should not be construed as limiting the invention. In this specification all temperatures are in degrees Centigrade, all parts are parts by weight, and all percentages are weight percentages unless otherwise expressly indicated.

EXAMPLE I 1097 grams of heads cut (AN 125.6) (40% Ca unsaps) was heated to 130° C. 71.6 grams of $Mg(OH)_2$ were added with good stirring. The reaction was fast and the water of reaction came off almost instantaneously. About 20 minutes was required to complete the reaction. Magnesium oxide gives a slower and more controlled reaction and is preferred to $Mg(OH)_2$.

The mass was slowly heated to 260° C. taking about 1 hour and a vacuum was slowly pulled on the system.

A standard laboratory vacuum distillation set up was used consisting of a stirred 3-neck flask fitted with a thermometer and take-off tube, a condenser, and a receiver.

A small amount of water vapor came off the reaction mass when the evacuation of the flask was started. Most of the unreacted material distilled over at 70–80 mm Hg pressure. The pressure was slowly reduced to 20 mm at which time distillation essentially was complete.

In this example, no recycle acids were added to the magnesium soap to lower the viscosity. It was allowed to cool to a solid at less than 100° C. and acidulated with dilute sulfuric acid. The acidulation of the Mg soap as a solid is slow, but was accomplished in about 2 hours.

---

687 grams of fatty acids, AN 188.7, unsaps 7.7%, color 18
367 grams of unsaps distilled over, AN 11.9
1054 grams total = 96% recovery of all products

---

Treating the recovered fatty acids with an absorptive clay at 90° C. for two hours, a common bleaching practice, and then stripping gave a distillate of 10–11 color (Gardner). Unsaps were 5–8% and 6% of the original charge remained behind as pitch.

The same operation without a clay bleach gave a color of 10–11 with 4% pitch, hence the recovered fatty acids are of low quality, but certainly of commercial value in applications where color is not of prime importance.

EXAMPLE II 356 grams of heads cut (AN 125.6, approximately 42% unsaps) were reacted with MgO in the manner set forth above in Example I at 230° C. in 3–4 minutes. (Later reactions will use a lower temperature to control the rapid evolution of water.) At 260° C. and 70 mm Hg pressure, the bulk of the unsaponifiable material was distilled off. Pressure was then lowered to 10 mm and temperature maintained until nothing more distilled. On cooling, the magnesium salt (308 g) was too viscous to pump so 73 grams of an unsaturated tall oil fatty acid was added. This gave a mixture that was of pumpable viscosity even at the nominal temperature of 100° C. In practice, it is anticipated that unsap free heads cut would be used instead of unsaturated fatty acids.

A 100-gram portion of the fatty acid was acidulated by heating and stirring with 15% sulfuric acid. The recovered fatty acid washed free of mineral acid had an acid number of 185.3 and contained 7.1% unsaps and weighed 94.5 grams.

119 grams of distillate were recovered from the initial mass. It had an AN of 36.1 (83% unsaps, calc.).

The acidulated soap was disappointingly high in unsaps and low in AN.

EXAMPLE III

The Sylvachem U.S. Pat. No. 4,064,117 yields high AN material after fusion with sodium or potassium hydroxide, stripping of the unsaps, and then acidulating the stripped fatty acid salts. Repeating this experiment with the available heads cut gave a final product of 207.5 AN.

It was believed that there might be an unexpected quality about sodium hydroxide which retarded the decarboxylation of heads cut at elevated temperatures.

To test this, 400 grams of heads cut (AN 125.6) were reacted with 23.5 g Mg(OH)$_2$ and 3.6 g of NaOH at 200° C. Vacuum stripping of the reaction product at 5 mm Hg pressure and a maximum pot temperature of 270° C. gave a soap which upon acidulation had an AN of 205.1. The distillate (39.3% of the charge) had an AN of 11.8.

EXAMPLE IV

Figure 2:
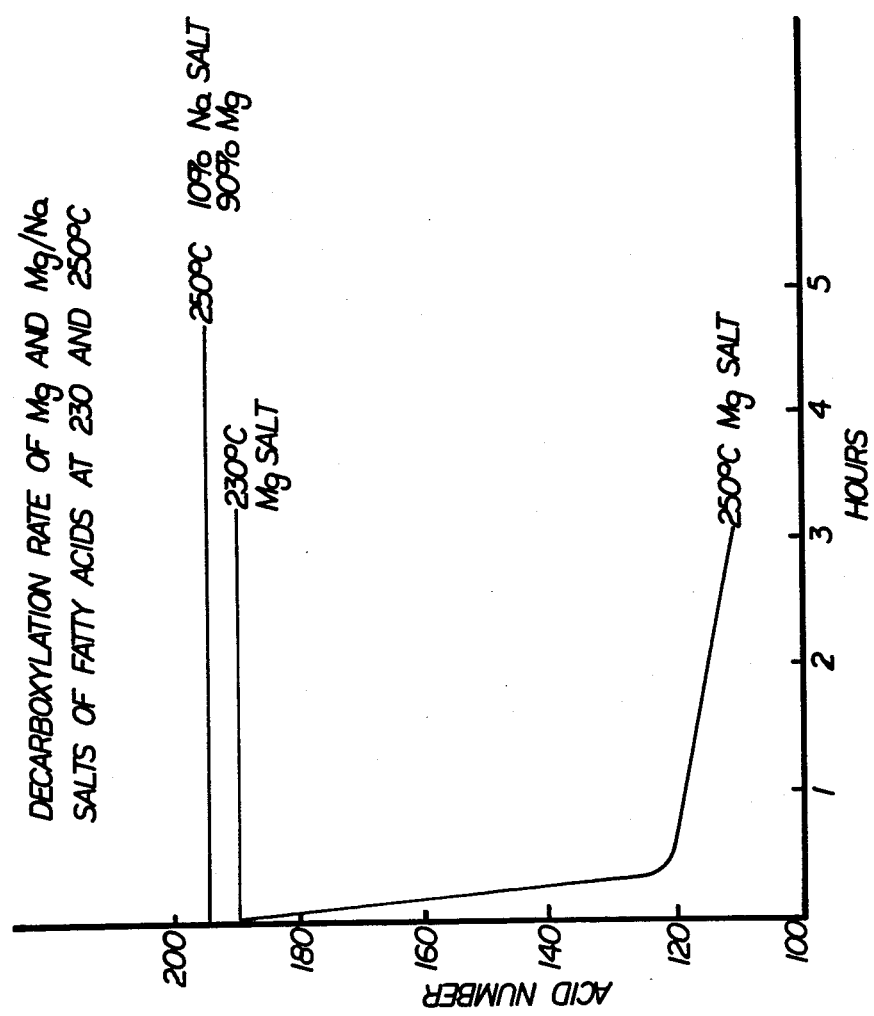
FIG. 2 is a graph showing decarboxylation rates at various temperatures for a mixed sodium/magnesium salts of heads fatty acids and the magnesium salts thereof.

To further indicate whether sodium hydroxide had a protective effect in the process, regular unsaturated tall oil fatty acids were reacted with an equivalent weight of Mg(OH)$_2$ and held at 250° C. Samples were periodically removed, acidulated and AN determinations made. Similarly, the procedure was followed with an equivalent weight reaction of fatty acids in which 90% neutralization of the acids group was effected with Mg(OH)$_2$ and the remaining 10% neutralized with NaOH. As can be seen from the annexed FIG. 2, the fatty acid magnesium salt decarboxylates rapidly at 250° C. while the 90% Mg/10% Na salt is quite stable at the same temperature.

The preferred mode of carrying out our invention is: Either simultaneously or concurrently:

1. React heads cut at 150°–200° C. with an amount of MgO (or Mg(OH)$_2$) to neutralize 50 to 90% of the heads cut acid units present. The remaining acid units are to be reacted with sodium or potassium hydroxide (or oxides). Strict adherence to stoichiometric amounts is not necessary. A quantity of base below the stoichiometric amount will result in a small yield of acidulated fatty acids and a greater quantity of acidic material lost to the overhead portions from the stripping; whereas a greater than stoichiometric amount will give higher yields of recovered acids and an overhead portion low in free acids. A grossly excessive quantity of MgO (or MgOH) so that the predominant chemical species is R—COOMgOH will result in a product of high viscosity which is very difficult to strip free of unsaponifiable material. Likewise, a reaction mass rich in sodium salts relative to Mg salts, while quite heat stable, will also be overly viscous. The ideal combination seems to be somewhere near the salt blend represented as 90 to 75% (RCOO)$_2$Mg and 10 to 25% R COO Na respectively.

MgO is preferred to Mg(OH)$_2$ for two reasons: (1) It is slower to react and presents less hazard from a boil-over; (2) It evolves a smaller quantity of water than Mg(OH)$_2$ and likewise presents less chance of boilover. All solids are carefully and slowly added to the hot heads cut with good mechanical stirring.

2. After the reaction is completed, a vacuum is carefully pulled on the flask. A small quantity of water is further evolved and the temperature increased and the vacuum slowly increased. The unsaps plasticize the Mg-Na salts. If too much unsaps are removed at a fairly low temperature, the reaction product will become too viscous. If this happens, the temperature should be increased to lower the viscosity. At the end of the stripping, for best results the temperature should not exceed 260° C. although brief excursions above this seem to do no harm and the pressure should be 20 mm Hg or less, preferably less than 5 mm. With 30 to 40% of the original mass removed as unsaps, the Mg-Na soaps are viscous and hard to pump if cooled to 230° C., so a quantity of fatty acids (preferably unsap free heads cut fatty acid) approximately equal to the quantity of unsaps removed by stripping is added to the molten salts at 230°–260° C. This provides a mixture that is pumpable even at 100° C. and also makes a product that acidulates easily because it is fluid.

3. Acidulation of the soap-fatty acid mixture is the normal procedure used for acidulation of crude tall oil, i.e., the soap is stirred at 90°–100° C. with dilute mineral acid (about 10–20% sulfuric is most commonly used). Acidulation is generally complete in 30 minutes. The pH of the water layer is maintained at 2 to 3.5 to assure complete acidulation. The final product may be washed or centrifuged to remove residual mineral acid.

What is claimed is:

1. A process for the recovery of fatty acids from tall oil heads which comprises the steps of neutralizing tall oil heads acids containing an unsaponifiable moiety with a mixture of from 75 wt. % to 95 wt. % of a magnesium soap-forming compound and from 5 wt. % to 25 wt. % of an alkali metal soap-forming compound under fusion conditions, stripping the unsaponifiable moiety at a temperature above about 230° C., springing the heads fatty acids with a mineral acid, and recovering the heads fatty acids.

2. A process as defined in claim 1 further characterized by the step of recycling a portion of the recovered heads fatty acid to the unsaponifiable stripped mixed magnesium/alkali metal soap for blending therewith to fluidize the soap stream.

3. A process as defined in claim 1 wherein the alkali metal is sodium.

4. A process as defined in claim 1 wherein the alkali metal soap-forming compound is selected from sodium hydroxide, potassium hydroxide, lithium hydroxide, sodium carbonate, potassium carbonate, lithium carbonate, sodium bicarbonate, potassium bicarbonate and lithium bicarbonate.

5. A process as defined in claim 1 wherein the magnesium soap-forming compound is selected from magnesium oxide, magnesium hydroxide and magnesium carbonate.

6. A process as defined in claim 1 wherein the mineral acid is sulfuric acid.

7. A process as defined in claim 1 wherein the temperature of fusion of the tall oil acids is in the range of from 160° C. to 300° C.

8. A process as defined in claim 7 wherein the reaction time is about 4 hours.

9. A process as defined in claim 1 wherein the water content of the initially formed reaction mixture is not greater than 12% by weight.

10. A process as defined in claim 1 wherein the water content of the initially formed reaction mixture is not greater than 8% by weight.

11. A process as defined in claim 1 wherein water is removed under reduced pressure from the reaction so that the water content of the reaction mass remains below about 12%.

* * * * *